United States Patent [19]

Steinkraus

[11] Patent Number: 4,626,508
[45] Date of Patent: Dec. 2, 1986

[54] **METHOD FOR EXTENDING THE VIABILITY OF VIRULENT *BACILLUS POPILLIAE***

[75] Inventor: Keith H. Steinkraus, Geneva, N.Y.

[73] Assignee: Cornell Research Foundation, Inc., Ithaca, N.Y.

[21] Appl. No.: 555,562

[22] Filed: Nov. 28, 1983

[51] Int. Cl.$^4$ .......... C12N 1/04

[52] U.S. Cl. .......... 435/242; 435/244; 435/248; 435/253; 435/260; 435/832

[58] Field of Search .......... 435/242, 253, 260, 832, 435/244, 248

[56] References Cited

U.S. PATENT DOCUMENTS

| | | | |
|---|---|---|---|
| 2,293,890 | 3/1940 | Dutky | 435/832 |
| 3,071,519 | 1/1963 | Bonnefoi | 435/242 |
| 3,087,865 | 4/1963 | Drake | 435/242 |
| 3,293,145 | 12/1966 | Leavitt et al. | 435/244 |
| 3,308,038 | 3/1967 | Rhodes et al. | 435/832 |
| 3,503,851 | 3/1970 | Srinivasan | 435/242 |
| 3,508,927 | 4/1970 | Herndon et al. | 435/244 |
| 3,616,250 | 10/1971 | Hrubant | 435/832 |
| 3,950,225 | 4/1976 | Skole et al. | 435/832 |

OTHER PUBLICATIONS

Bulla et al, Journal of Bacteriology (1970), vol. 104, No. 3, pp. 1246–1253.

The Condensed Chemical Dictionary, 10th ed., Oct. 14, 1983, Van Nostrand Reinhold Co. Inc., N.Y., p. 282.

Foster et al, Journal of Bacteriology (1948), vol. 55, pp. 495–500.

The Condensed Chemical Dictionary, 8th ed., Van Nostrand Reinhold Co., N.Y., pp. 518–519.

Bennett et al, *Insect Physiol.*, vol. 18, pp. 53–62 (1972).

Bennett et al, *J. Invertebrate Path.*, 15: 157–164 (1970).

*Primary Examiner*—Sam Rosen

*Assistant Examiner*—William J. Herald

[57] ABSTRACT

This invention relates to the incorporation of $C_{16}$ to $C_{20}$ unsaturated fatty acids into in vitro growth media of milky disease bacilli, e.g. *Bacillus popilliae*, to extend culture viability and/or promote sporulation.

10 Claims, No Drawings

METHOD FOR EXTENDING THE VIABILITY OF VIRULENT *BACILLUS POPILLIAE*

BACKGROUND OF THE INVENTION

Certain microorganisms are natural pathogens/parasites for Japanese beetles, European chafers and related insects belonging to Family *Scarabaeidae*. There are over 19,000 species of beetles belonging to Family *Scarabaeidae*. Wherever the beetles occur in large populations, milky disease bacilli have been found naturally infecting portions of the populations. There are now about 12 distinct morphological types of bacilli that cause milky disease in one beetle species or another. They are all rod shaped in the reproductive stage and form spores in the resistant dormant stage. Some such as *B. popilliae* contain a parasporal body. Some do not contain parasporal body and, in some cases, the spore is smaller than a parasporal body in *B. popilliae*. In all cases, the spores are ingested by healthy larvae, germinate either in the gut or gut tissues possibly aided by lymphocytes, multiply in the tissues or in the hemolymph and eventually sporulate in the tissues or hemolymph. Only after cell/spore populations have reached to the billions/ml of hemolymph does the host die and release its spore load into the soil where the spores remain dormant (but alive) until consumed by a susceptible host to repeat the cycle. Scientists have been studying *Bacillus popilliae* and other milky disease bacilli for the last 40 to 45 years. It was recognized very early that these bacilli offered a potential method for biological control of the beetles. Dr. S. R. Dutky of the U.S.D.A. obtained a patent (U.S. Pat. No. 2,293,890) on a process of producing the spores of *Bacillus popilliae* by injecting the bacilli into Japanese beetle larvae, allowing the bacilli to complete their life cycle including formation of spores and then grinding the diseased larvae with a diluent such as talc. The resultant spore dust was inoculated into the soil and served as a means of infecting and controlling succeeding populations of Japanese beetles and European chafers that might have invaded the area. Further patents dealing with the production of *B. popilliae* as microbial insecticides includes U.S. Pat. Nos. 3,308,038; 3,503,851; 3,616,250 and 3,950,225. While spores produced by the in vivo process have been on the market for a number of years, the method is handicapped by the necessity of collecting and inoculating thousands of larvae each year.

For the past 25 to 30 years, scientists have been endeavoring to elucidate the factors controlling sporulation in vivo and particularly in vitro with the objective of developing methods of producing the spores en masse in vitro. Steinkraus and Tashiro (Science. 1955. Vol. 121:873-874) produced spores of *B. popilliae* in vitro by growing the vegetative cells on the surface of a suitable growth medium and then transferring the cells as a paste to the surface of a "starvation" medium on which further vegetative growth was impossible. While this in vitro method of producing spores yielded sufficient spores to establish that the spores were virulent when fed to or injected into healthy European chafer larvae, it was strain related, difficult to reproduce repeatedly on a large scale and therefore was impractical commercially.

Subsequently, the U.S. Department of Agriculture undertook an expanded research program on the in vitro production of spores of *B. popilliae*. The USDA developed strains of *B. popilliae* that formed spores in vitro under certain conditions. In all cases, particular strains were required. Some of the methods required the use of specific batches of ingredients. However, in contrast to the method of Steinkraus and Tashiro, above, either the USDA method failed to produce sufficient spores to test or when tested, the spores were no longer virulent per os. And, in no case, up to the present, (including the Steinkraus and Tashiro method) was the factor or factors controlling sporulation apparent.

The Steinkraus and Tashiro method depended upon cultivation of the vegetative cells and the sporulation phase both on the surface of solid media.

The USDA methods also used the surfaces of solid media in some cases but tried to cultivate the vegetative cells in submerged culture as this procedure is more adaptable to large scale commercial production of vegetative cells and spores. Unfortunately, in submerged culture, the cells of *B. popilliae* tend to grow to a peak population in less than 20 hours and then they die very rapidly. Dead vegetative cells, of course, will not sporulate.

R. Skole and A. B. Rizzuto obtained U.S. Pat. No. 3,950,225 which described a process whereby vegetative cells of *B. popilliae* grown on a suitable medium sporulated when suspended in bone char waste water. The present inventor has confirmed that vegetative cells derived from germinated spores removed from milky diseased larvae and grown on a suitable medium do sporulate when circulated through bone char columns under certain conditions. The factor or factors controlling sporulation in the bone char have not been elucidated. The mechanism could be removal of substances inhibiting sporulation or concentration of cells or substances required for sporulation or both. It was found necessary to grow the vegetative cells of *B. popilliae* on the surface of agar plates in pure culture, suspend them in a mineral salts medium that resembles char waste water and circulate them through the bone char column in order to obtain sporulation. Attempts to use submerged cultivation of the cells highlighted of the difficulty of maintaining cell viability from time of growth to time of circulation through the column. The Skole and Rizzuto patented method does not reveal the essential factor or factors controlling sporulation of *B. popilliae*.

Sporulation of milky disease bacilli in vitro has been studied intensively for 30 years, yet the factors controlling sporulation in vitro or in vivo remain unknown. Bennett and Shotwell (1970, J. Invert. Path. 15:157-164) reported that the content of $C_{16}$-$C_{22}$ unsaturated fatty acids in hemolymph decreased markedly during the course of milky disease. They further suggested (J. Insect Physiology (1972) 18:53-62) that lipids might be altering membrane permeability (of the bacilli) and influencing enzyme activity related to sporulation. Bulla, Bennett and Shotwell (1970, J. Bact. 104:1246-1253) recognized that the lipid components might be playing an important role in growth and sporulation of *B. popilliae* but apparently none of the studies were tied directly into sporulation either in vivo or in vitro.

There is virtually nothing in the sporulation literature that would suggest that fatty acids might play an important role. In fact, there is evidence in the published literature that would suggest that fatty acids are inhibitory to sporulation, Humfeld (1974, J. Bact. 54:513-517) reported an "antibiotic-like" activity for $C_{18}$ fatty acids extracted from wheat bran. Gram-positive cocci were inhibited but Gram-negative *Escherichia coli* was not. Foster and Wynne (1948, J. Bact. 55:495–50) reported that the $C_{18}$ unsaturated fatty acids, particularly oleic inhibited growth of a wide-range of bacteria including *Clostridium botulinum*, an anaerobic sporeformer. They reported that small amounts of oleic, linoleic and linolenic acids inhibited germination of spores of *C. botulinum* and that addition of 0.1% soluble starch eliminated the inhibition. Wynne and Foster also reported that the addition of 0.1% soluble starch to pork infusion thioglycollate broth increased germination of *C. botulinum* thirty times.

The studies of Humfeld and Wynne and Foster are of interest in retrospect because it had been reported earlier (Lehrman, 1929) that rice starch contained 14.75 grams of mixed unsaturated fatty acids/5 lbs of rice starch; and Taylor and Lehrman reported (1926, J. Am. Chem. Soc. 48:1739–1743) that corn starch contains 0.5 to 0.6% unsaturated fatty acids.

DESCRIPTION OF THE INVENTION

This invention relates to the discovery that $C_{16}$ to $C_{20}$ ethylenically unsaturated fatty acids significantly extend the viability of cultures of milky disease bacilli, where virulent spores, especially *B. popilliae* are inoculated into suitable media. When maintained in the presence of suitable growth aqueous media containing the fatty acid the cultures remain viable for significant periods in excess of the periods observed absent the fatty acid, and sporulation resembling that observed in vivo occurs in vitro.

One object of this invention is to provide a method for the production of milky disease bacilli spores in large quantities.

Another object of this invention is to provide in vitro culture methods which extend life of vegetative milky disease cultures and/or which produce milky disease bacilli cells/spores.

These and other desirable objects and advantages are obtained by incorporation of a milky disease bacilli culture viability extending or milky disease bacilli sporulation enhancing amount of a $C_{16}$–$C_{20}$ ethylenically unsaturated fatty acid into a culture medium adapted to support the vegetative cultivation of the milky disease bacilli.

The presently preferred amount of unsaturated fatty acid is about 0.1% to about 0.5% by weight of the medium. The presently preferred acid is linoleic acid. The term "unsaturated fatty acid" includes mixtures thereof.

While the growth supporting medium can be a solid or semisolid medium, for example an agar based medium, it is highly preferable that the medium be a conventional liquid nutrient medium adapted for submerged culture. Suitable media, and especially aqueous liquid media, for the cultivation milky disease bacilli are known to those skilled in the art. A particularly preferred aqueous medium for use in the process of the present invention comprises, in addition to the unsaturated fatty acid:

Mueller Hinton Peptone (Difco)—1% w/v
Yeast Extract (Difco)—1% w/v
$K_2HPO_4$—0.3% w/v
Pyruvate—0.1% w/v
pH 7.2

When the above medium, containing 0.1 to 0.5% linoleic acid, is inoculated with $10^6$ spores/ml of virulent spores of *B. popilliae*, the spores germinate, followed by outgrowth of vegetative cells, followed by sporulation. The cells/spores remain viable for at least 90 days and during this period, there is some evidence that there are cycles of germination and vegetative cell multiplication followed by sporulation. It has been noted that amounts of linoleic acid in the order of 1% to 2% by weight of the above media cause reduction of spore formation.

It is highly preferred that the fatty acid containing growth medium be inoculated with virulent spores.

The milky disease bacilli spores can be harvested from the culture medium and inoculated into the soil using conventional practices and equipment. Or the spores may be concentrated by spray drying and subsequently reconstituted into a desired formulation prior to use.

Since the milky disease vegetative cells/spores derived from the above described culture processes have extended viability, the resultant culture is useful as a source of cells/spores to be inoculated into the char waste water sporulation process described in U.S. Pat. No. 3,950,225.

In yet another alternative aspect of this invention comprises the presence of a sporulation enhancing amount of a $C_{16}$–$C_{20}$ ethylenically unsaturated fatty acid in the process described in U.S. Pat. No. 3,950,225 (hereby incorporated by reference in its entirety). This process comprises the use of char waste water as a component of a medium for the sporulation of spore producing milky disease bacilli, namely *B. popilliae*. Char waste water is a waste product of sugar refining, such as cane sugar refining. In the refining of cane sugar, animal charcoal (char), such as bone char, which is the granular residue obtained by destructive distillation, is employed. In the processing of sugar liquors or syrups, after clarification by defecation, the remaining color bodies and other impurities in the sugar syrups or liquors must be removed before a satisfactory refined crystallized sugar is produced. These color bodies and other impurities are removed from the defecated, filtered sugars and liquors by percolation and filtration of the sugar syrup and liquors through cisterns or tanks filled with animal charcoal (char). After the ability of the char to remove color and other impurities from the sugar syrups and liquors undergoing treatment by contact with the char is diminished, the char cisterns or filters are "sweetened off" or washed with hot water. After 12 to 14 hours washing, the sugar content of the resulting wash water is no longer sufficient to warrant recovery of sugar containing water. At that time, the wash water is usually turned to waste, the washing of the char to waste continuing for about 12–24 hours, more or less, usually about 14–18 hours. During this period of washing the char to waste, there is produced the char waste water useful in producing this segment of the invention analysis of typical char waste waters and ranges for the components are set forth in U.S. Pat. No. 3,950,225.

A typical chemical analysis of bone char is substantially as follows: carbon 8.5–10, insolubilized ash 0.2, sulfate (as $CaSO_4$) 0.08, sulfide (as CaS) 0.07, carbonate (as $CaCO_3$) 7.9, iron 0.07, phosphate (as $CaPO_4$) 80.6–84.1.

In the practice of this segment of the invention, the char waste water need not be a composite of the total char waste water. Char waste water collected at various times during the water washing operation produces char waste water satisfactory for use in a sporulation process within the scope of this invention.

It is noted that apparently char waste water in at least some instances may contain at least some amounts of unsaturated fatty acids which may account for the fact that the inventors in U.S. Pat. No. 3,950,225 found that char waste water was a useful sporulation media. However U.S. Pat. No. 3,950,225 never identified a fatty acid content or recognized any need for the presence of unsaturated fatty acids. This alternative embodiment of the invention comprises adjusting the $C_{16}$–$C_{20}$ ethylenically unsaturated fatty acid content of a sporulation medium comprising char waste water to provide a sporulation medium containing a sporulation enhancing amount of a $C_{16}$–$C_{20}$ unsaturated fatty acid.

The adjustment can be accomplished in two distinct manners. Where a char waste water is devoid of or contains less than a desired amount of said fatty acid, an appropriate amount of said fatty acid can be added to the char waste water to provide a desired sporulation enhancing amount of $C_{16}$–$C_{20}$ unsaturated fatty acid. Alternatively, should the char waste water contain $C_{16}$–$C_{20}$ fatty acid in excess of a desired amount of said fatty acid the char waste water can be diluted with water to adjust the fatty acid content to an appropriate desired amount of fatty acid.

With the exception of the above adjustment the alternative sporulation process of the invention comprise that described in U.S. Pat. No. 3,950,225.

While the processes of this invention have been exemplified as applicable to the production of spores of *B. popilliae*, this invention is generally applicable to the production of milky disease bacilli vegetative cells/spores, including, but not limited to, *Bacillus lentimorbus* and related bacilli producing milky disease in *Scarabaeid* beetle larvae and related insects.

I claim:

1. In a method for extending the viability of an in vitro culture of *Bacillus popilliae* in a growth supporting medium the improvement comprising adding to the growth supporting medium a culture viability extending amount of $C_{16}$–$C_{20}$ ethylenically unsaturated fatty acid.

2. The method of claim 1 where the culture medium is a liquid aqueous medium.

3. The method of claim 2 where the acid is linoleic acid.

4. In a method for enhancing the sporulation of an in vitro culture of *Bacillus popilliae* in a growth supporting medium the improvement comprising adding to the milky growth supporting medium a sporulation enhancing amount of $C_{16}$–$C_{20}$ ethylenically unsaturated fatty acid.

5. The method of claim 4 where the culture medium is a liquid aqueous medium.

6. The method of claim 5 where the acid is linoleic acid.

7. In a method of sporulating *Bacillus popilliae* in char waste water which may or may not contain unsaturated fatty acid the improvement comprising adjusting the content of $C_{16}$–$C_{20}$ ethylenically unsaturated fatty acid to provide a sporulation enhancing amount of said acid.

8. The method of claim 7 where fatty acid is added to the char waste water.

9. The method of claim 7 where the fatty acid is linoleic acid.

10. The method as in claims 1, 2, 3, 4, 5 or 6 wherein the growth supporting medium is inoculated with virulent spores of *B. popilliae*.

* * * * *